United States Patent
Himmler et al.

(10) Patent No.: US 6,995,170 B1
(45) Date of Patent: Feb. 7, 2006

(54) SEMI-HYDROCHLORIDE OF 8-CYANO-1-CYCLOPROPYL-7-(1S,6S-2,8-DIAZA-BICYCLO[4.3.0]NONAN-8-YL)-6-FLUORO-1,4-DIHYDRO-4-OXO-3-QUINOLINE-CARBOXYLIC ACID

(75) Inventors: Thomas Himmler, Odenthal (DE); Hubert Rast, Leverkusen (DE)

(73) Assignee: Bayer Aktiengesellschaft, Leverkusen (DE)

(*) Notice: Subject to any disclaimer, the term of this patent is extended or adjusted under 35 U.S.C. 154(b) by 0 days.

(21) Appl. No.: 09/856,571

(22) PCT Filed: Nov. 15, 1999

(86) PCT No.: PCT/EP99/08778

§ 371 (c)(1),
(2), (4) Date: May 23, 2001

(87) PCT Pub. No.: WO00/31077

PCT Pub. Date: Jun. 2, 2000

(30) Foreign Application Priority Data

Nov. 25, 1998 (DE) .................. 198 54 357

(51) Int. Cl.
*A61K 31/44* (2006.01)
*C07D 471/02* (2006.01)

(52) U.S. Cl. .................. 514/300; 546/113

(58) Field of Classification Search ............ 546/113; 514/300

See application file for complete search history.

(56) References Cited

FOREIGN PATENT DOCUMENTS

WO     WO 9731001    * 8/1997

* cited by examiner

*Primary Examiner*—Cecilia J. Tsang
*Assistant Examiner*—Binta Robinson
(74) *Attorney, Agent, or Firm*—Susan M. Pellegrino

(57) ABSTRACT

The present invention relates to a semi-hydrochloride of 8-cyano-1-cyclopropyl-7-(1S,6S-2,8-diazabicyclo[4.3.0]nonan-8-yl)-6-fluoro-1,4-dihydro-4-oxo-3-quinoline-carboxylic acid, to processes for its preparation and to antibacterial compositions comprising it. The semihydrochloride of 8-cyano-1-cyclopropyl-7-(1S,6S-2,8-diazabicyclo[4.3.0]nonan-8-yl)-6-fluoro-1,4-dihydro-4-oxo-3-quinolinecarboxylic acid can be described by the following formula:

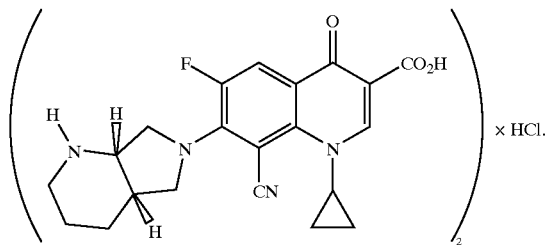

19 Claims, 6 Drawing Sheets

Fig. 3 CCDC-Hydrochlorid

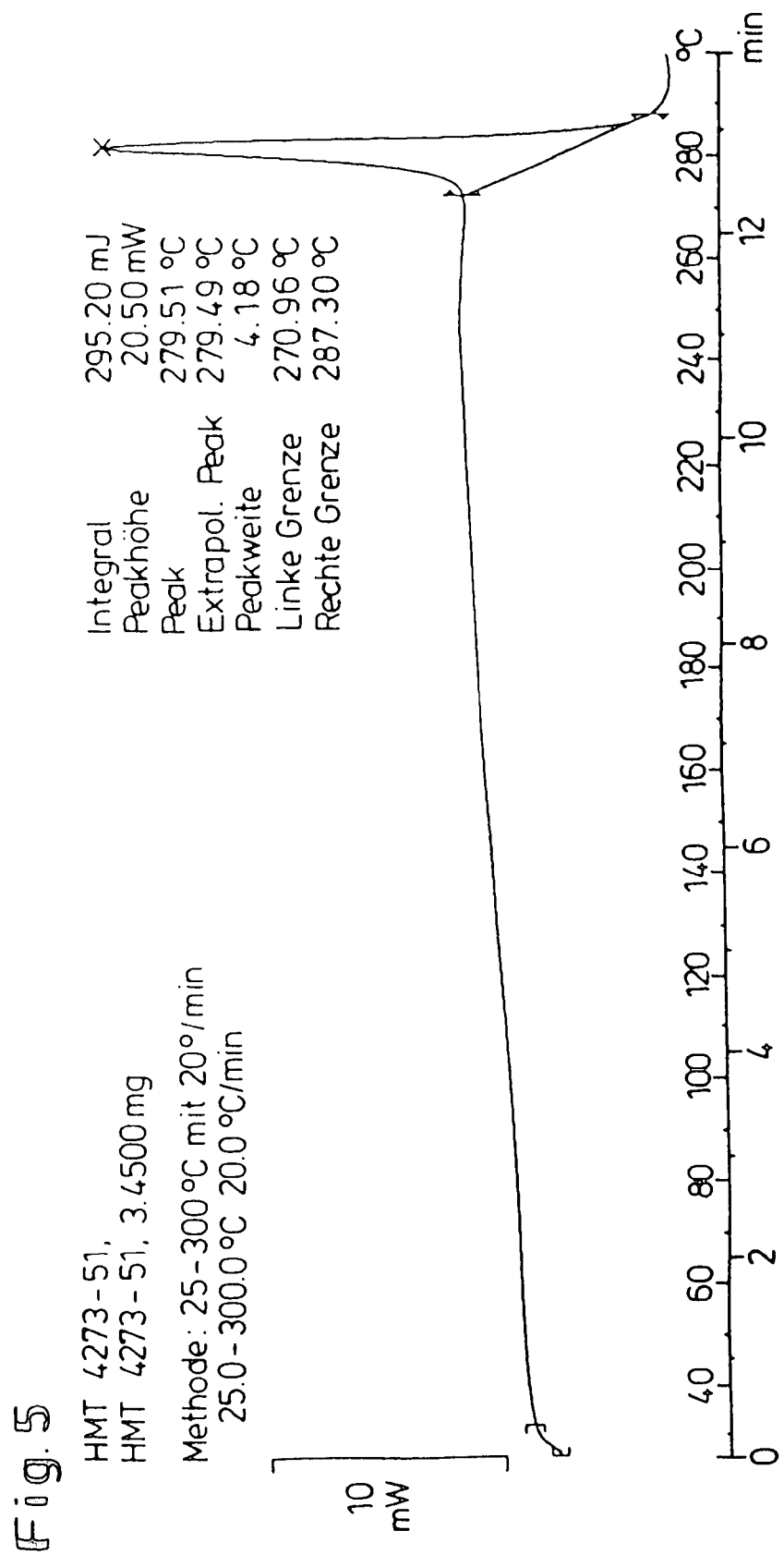

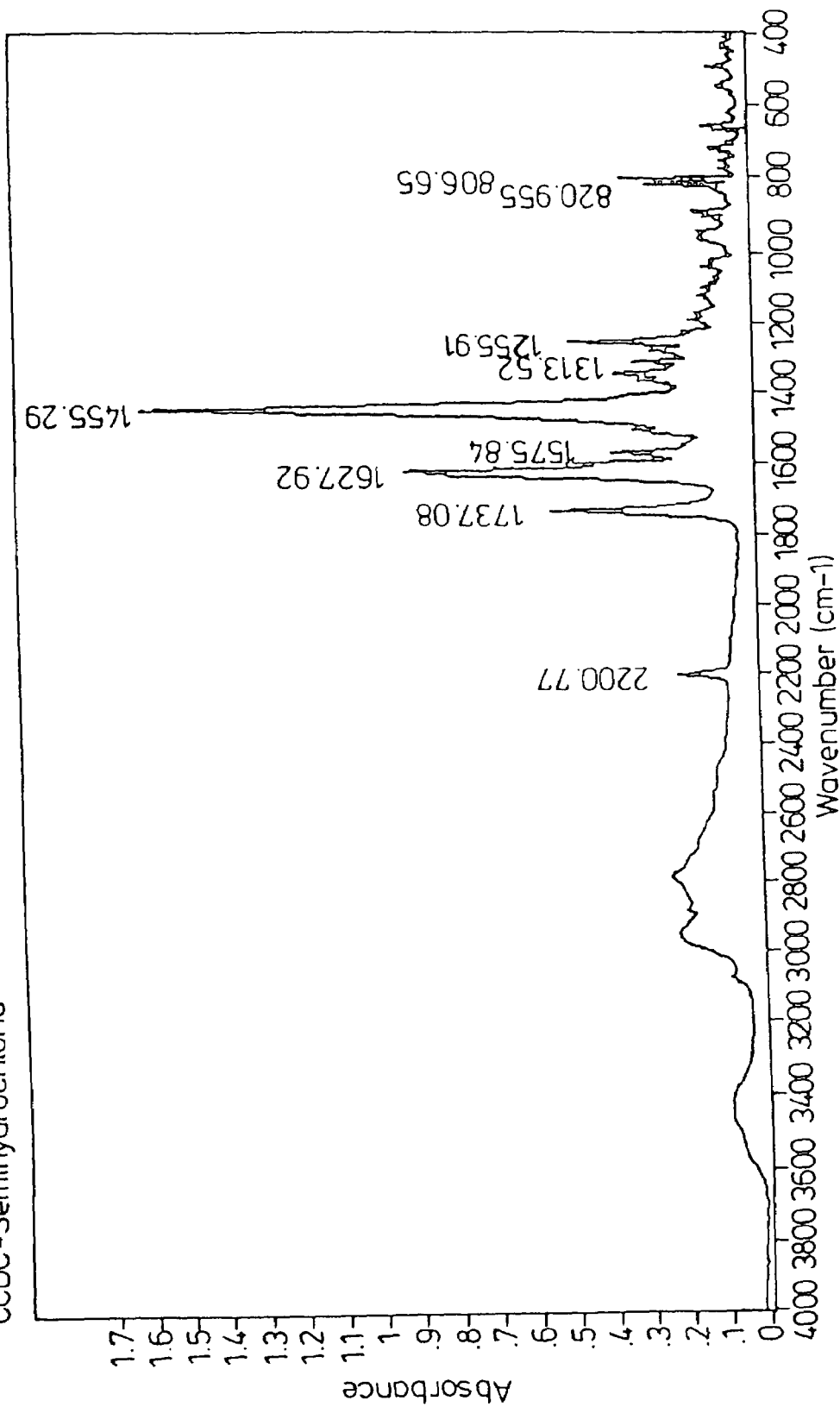
Fig. 6 CCDC-Semihydrochlorid

SEMI-HYDROCHLORIDE OF 8-CYANO-1-CYCLOPROPYL-7-(1S,6S-2,8-DIAZA-BICYCLO[4.3.0]NONAN-8-YL)-6-FLUORO-1,4-DIHYDRO-4-OXO-3-QUINOLINE-CARBOXYLIC ACID

The present invention relates to a semi-hydrochloride of 8-cyano-1-cyclopropyl-7-(1S,6S-2,8-diazabicyclo[4.3.0]nonan-8-yl)-6-fluoro-1,4-dihydro-4-oxo-3-quinoline-carboxylic acid, to processes for its preparation and to antibacterial compositions comprising it. 8-Cyano-1-cyclopropyl-7-(1S,6S-2,8-diazabicyclo[4.3.0]nonan-8-yl)-6-fluoro-1,4-dihydro-4-oxo-3-quinolinecarboxylic acid of the formula (I) is to be referred to as CCDC hereinbelow.

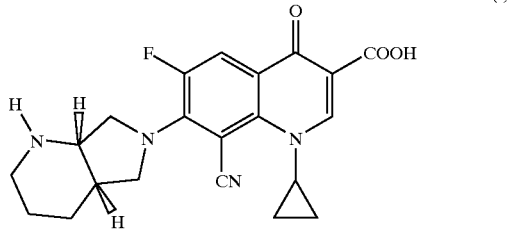
(I)

CCDC is known from DE-A 19 633 805 or PCT Appl. No. 97 903 260.4. It is prepared by reacting 7-halogeno-8-cyano-1-cyclopropyl-6-fluoro-1,4-dihydro-4-oxo-3-quinolinecarboxylic acid of the formula (II)

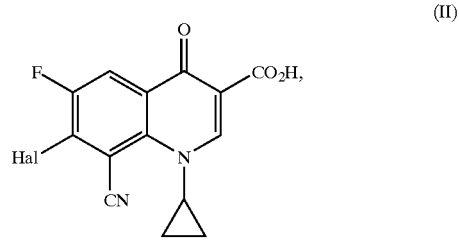
(II)

in which

Hal represents fluorine or, preferably, represents chlorine with (1S,6S)-2,8-diazabicyclo[4.3.0]nonane of the formula (III)

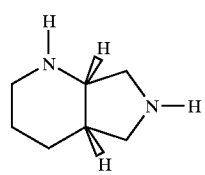
(III)

in the presence of an auxiliary base in a suitable solvent.

CCDC of the formula (I) can be used to prepare solutions in water of about 0.02% strength (w/w). For pracitical applications (solutions for injections or oral administration forms), this solubility is insufficient. Many other quinolonecarboxylic acids are known to be used for formulations in the form of certain salts. Salts which are suitable for this purpose are, on the one hand, metal salts of quinolonecarboxylic acid (for example alkali metal carboxylates) and, on the other hand, acid addition products (protonation of basic centres in the amine radical of the substituted quinolonecarboxylic acids). Acid addition products which are frequently used are, for example, mesylates, tosylates and hydrochlorides. Hydrochlorides can be prepared in a particularly simple manner, they are pharmaceutically acceptable and they have considerably better solubilities than the neutral compounds.

The CCDC hydrochloride of the formula (IV)

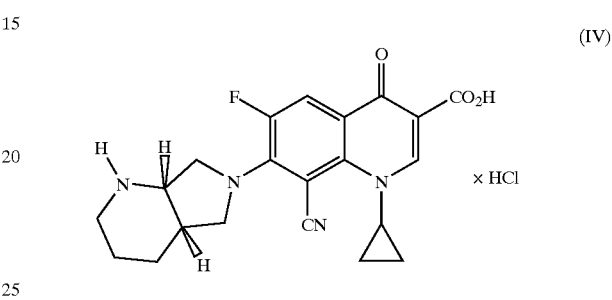
(IV)

is known from WO 97/31001.

It can be characterized by its X-ray powder diffractogram, by differential thermoanalysis (DTA) and by its infrared spectrum (IR).

The X-ray powder diffractogram has the reflection signals (2 theta) of high and medium intensity (>30% relative intensity) shown in Table 1.

TABLE 1

| X-Ray powder diffractogram of CCDC hydrochloride of the formula (IV) |
| --- |
| 2θ (2 theta) |
| 6.70 |
| 13.11 |
| 15.63 |
| 25.69 |
| 25.90 |

The X-ray powder diffractogram of CCDC hydrochloride of the formula (IV) is also shown in FIG. 1.

The melting point, determined by DTA, of CCDC hydrochloride of the formula (IV) is from 305° C. to 307° C. (with decomposition). The differential thermodiagram is shown in FIG. 2.

The IR spectrum of CCDC hydrochloride of the formula (IV) is shown in FIG. 3.

CCDC hydrochloride of the formula (IV) can be prepared by methods which are known in principle. Thus, it is possible, for example, to admix a solution of CCDC of the formula (I) in water with a molar equivalent of HCl and to evaporate the solution to dryness. Another method consists in hydrolyzing ethyl 8-cyano-1-cyclopropyl-7-(1S,6S-2,8-diazabicyclo[4.3.0]nonan-8-yl)-6-fluoro-1,4-dihydro-4-oxo-3-quinoline-carboxylate of the formula (V)

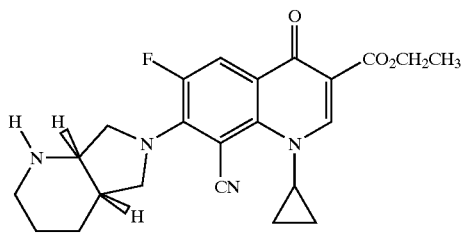

(V)

in aqueous hydrochloric acid and to isolate the precipitated CCDC hydrochloride of the formula (IV).

CCDC hydrochloride of the formula (IV) can be used to prepare a solution in water of a strength of approximately 2.8% (w/w). Thus it is more readily water-soluble than CCDC of the formula (I), but not to an extent which is desirable for all formulations.

According to the invention, it has been found that, surprisingly, the CCDC semihydrochloride of the formula (VI)

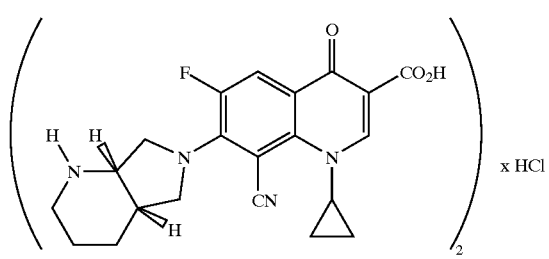

(VI)

has a particularly high solubility in water. CCDC semihydrochloride of the formula (VI) can be used to prepare solutions in water having a strength of 19% (w/w).

The invention accordingly provides crystalline CCDC semihydrochloride of the formula (VI) which is, inter alia, characterized in that it has an X-ray powder diffractogram with the reflection signals of high and medium intensity (>30% relative intensity) given in Table 2.

TABLE 2

X-Ray powder diffractogram of CCDC semihydrochloride of the formula (VI)

| 2 θ (2 theta) |
|---|
| 5.86 |
| 6.90 |
| 7.26 |
| 8.98 |
| 9.35 |
| 10.13 |
| 10.68 |
| 10.97 |
| 12.41 |
| 13.67 |
| 14.57 |
| 14.89 |
| 15.73 |
| 16.07 |
| 16.47 |
| 16.87 |
| 17.78 |

TABLE 2-continued

X-Ray powder diffractogram of CCDC semihydrochloride of the formula (VI)

| 2 θ (2 theta) |
|---|
| 18.91 |
| 19.81 |
| 20.04 |
| 20.62 |
| 20.75 |
| 20.93 |
| 21.46 |
| 21.74 |
| 22.92 |
| 25.36 |
| 25.71 |
| 26.98 |
| 27.58 |
| 28.24 |
| 30.61 |

BRIEF DESCRIPTION OF THE DRAWINGS

FIG. 5 shows the differential thermodiagram of CCDC semihydrochloride of formula (VI) obtained by the procedure of Example 1, having a melting point of 278 to 280° C. determined by differential thermoanalysis.

FIG. 6 shows the IR spectrum, measured in KBr of the CCDC semihydrochloride of the formula (VI).

Figure 4:
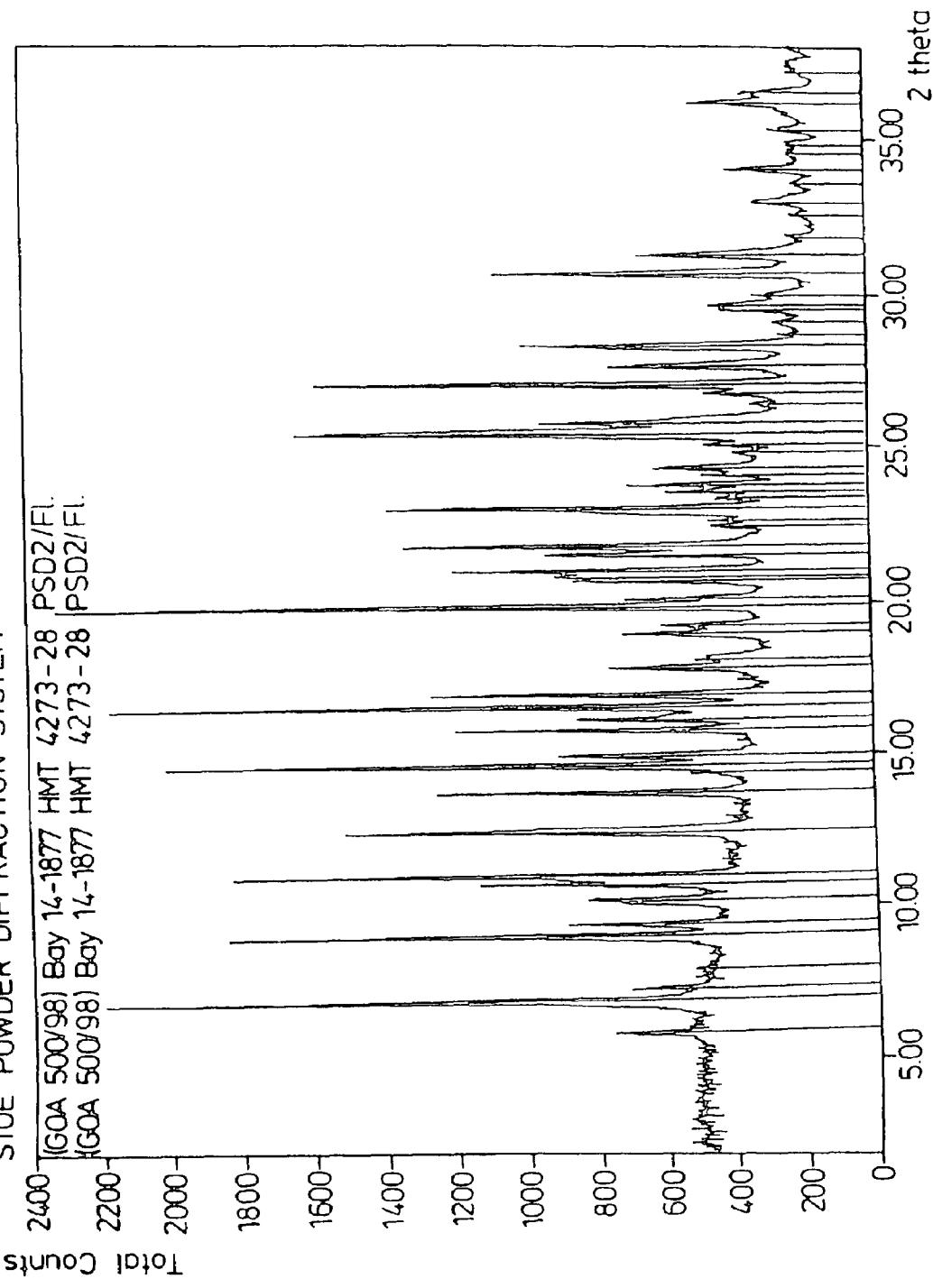
FIG. 4 shows the X-ray powder diffractogram of CCDC semihydrochloride of the formula (VI).

The X-ray powder diffractogram of CCDC semihydrochloride of the formula (VI) is shown in FIG. 4.

The CCDC semihydrochloride of the formula (VI) is furthermore characterized in that it has a melting point, determined by differential thermoanalysis, of from 278° C. to 280° C. The corresponding differential thermodiagram is shown in FIG. 5.

The CCDC semihydrochloride of the formula (VI) according to the invention is furthermore characterized in that it has an infrared spectrum, measured in KBr, as shown in FIG. 6.

CCDC semihydrochloride of the formula (VI) of an undetermined crystal form can be prepared by processes known in principle, for example by admixing a solution of CCDC of formula (I) in water with half a molar equivalent of HCl and evaporating the solution to dryness.

Likewise, it is possible in principle to admix such amounts of CCDC of the formula (I) and CCDC hydrochloride of the formula (IV) in a molar ratio of one to one in water such that the total concentration remains less than 20%. The resulting solution can subsequently be evaporated to dryness.

Moreover, it has been found according to the invention that, surprisingly, a CCDC semihydrochloride of the formula (VI) which is characterized by the X-ray powder diffractogram shown above and the differential thermodiagram shown above can be prepared directly.

The present invention therefore furthermore provides the CCDC semihydrochloride of the formula (VI) which is characterized in that 7-halogeno-8-cyano-1-cyclopropyl-6-fluoro-1,4-dihydro-4-oxo-3-quinolonecarboxylic acid of the formula (II), in which halogen represents fluorine or, preferably, represents chlorine, is reacted with (1S,6S)-2,8-diazabicyclo[4.3.0]nonane of the formula (III), if appropriate in the presence of a base, in one of the following diluents or diluent mixtures:

a) aliphatic alcohols having at least four carbon atoms, such as, for example, butanol, isobutanol, 2-butanol, tert-butanol, 1-pentanol, b) mixture of aliphatic alcohols having at least three carbon atoms such as, for example, propanol, isopropanol, butanol, isobutanol, 2-butanol, tert-butanol or 1-pentanol, with the polar aprotic solvent N-methylpyrrolidone, c) mixture of propanol and N,N-dimethylformamide, or d) mixture of ethanol with N-methyl-pyrrolidone with added tertiary amine base, such as, for example, tripropylamine, tributylamine, N-ethylmorpholine, N-propylmorpholine and/or N-butylmorpholine.

In the preferred preparation variants with a diluent mixture according to b) or c), the mixing ratio is from 1:1 to 3:1 and, in particularly preferred embodiments, from 1:1 to 2:1.

Suitable bases according to the preparation variants with the diluents and the diluent mixtures according to a) to c) are tertiary amines, such as, triethylamine, tripropylamine, ethyl-diisopropylamine (Hünig base), tributylamine, N-ethylmorpholine, N-propylmorpholine and N-butylmorpholine.

In the preparation variants a) to d), preference is given to those embodiments where an excess of (1S,6S)-2,8-diazabicyclo[4.3.0]nonane of the formula (III) is employed.

In the preparation variants according to a) to d), preferably from 1 to 2 mol of base, particularly preferably from 1.1 to 1.5 mol of base, are employed per mole of the compound (II).

The reaction in the preparation variants according to a) to d) is carried out at atmospheric pressure or at elevated pressure between 1 bar and 100 bar, preferably between 1 bar and 20 bar.

The reaction in the preparation variants according to a) to d) is carried out at temperatures between 0° C. and 200° C., preferably between 20° C. and 150° C.

Preferably from 1 to 2 mol, particularly preferably from 1 to 1.5 mol, of the compound (III) are employed per mole of the compound (II).

CCDC semihydrochloride of the formula (VI) precipitates out of the reaction mixture and can be filtered off with suction. The solid which has been filtered off with suction can, if appropriate, be purified by washing with the alcohol used in the reaction.

The starting materials of the formulae (II) and (III) for preparing CCDC are known (cf. DE-A 19 633 805).

CCDC semihydrochloride of the formula (VI) is highly active against pathogenic bacteria in the area of human or veterinary medicines. Its broad area of use corresponds to that of CCDC.

The X-ray powder diffractogram for characterizing the crystal modifications of CCDC hydrochloride and CCDC semihydrochloride were obtained using a transmission diffractiometer STADI-P with location-sensitive detector (PSD2) from Stoe.

The melting point of the differential thermoanalysis was obtained using the DSC 820 unit from Mettler-Toledo. The sample was heated in the air in an aluminium crucible using 20 K/min.

The IR spectrum was recorded in KBr using the FTS 60 A unit from Biorad.

The examples below illustrate the invention without limiting it. The diluents/base systems described in the examples below are particularly preferred.

Comparative Example

Preparation of CCDC hydrochloride of the formula (IV)

850 g of ethyl 8-cyano-1-cyclopropyl-7-(1S,6S-2,8-diazabicyclo[4.3.0]nonan-8-yl)-6-fluoro-1,4-dihydro-4-oxo-3-quinolinecarboxylate are initially charged in a mixture of 1600 ml of water and 800 ml of 10% strength hydrochloric acid. The reaction mixture is heated to the boil, with the ester going into solution and the product soon beginning to precipitate out. The suspension is heated at the boil for 3 hours. It is then allowed to cool to approximately 50° C., and 1500 ml of ethanol are added. The reaction mixture is cooled to 0° C. and stirred at this temperature for 1 hour. The solid is filtered off with suction, washed with 1000 ml of ethanol and dried at 60° C. until the weight remains constant. This gives 845.5 g of a beige solid.

Elemental analysis (calculated values for the hydrochloride $C_{21}H_{22}ClFN_4O_3$, molecular weight 432.89):

Carbon: found 58.2% (calc. 58.27%)

Hydrogen: found 5.1% (calc. 5.12%)

Chlorine: found 8.1% (calc. 8.19%).

Figure 1:
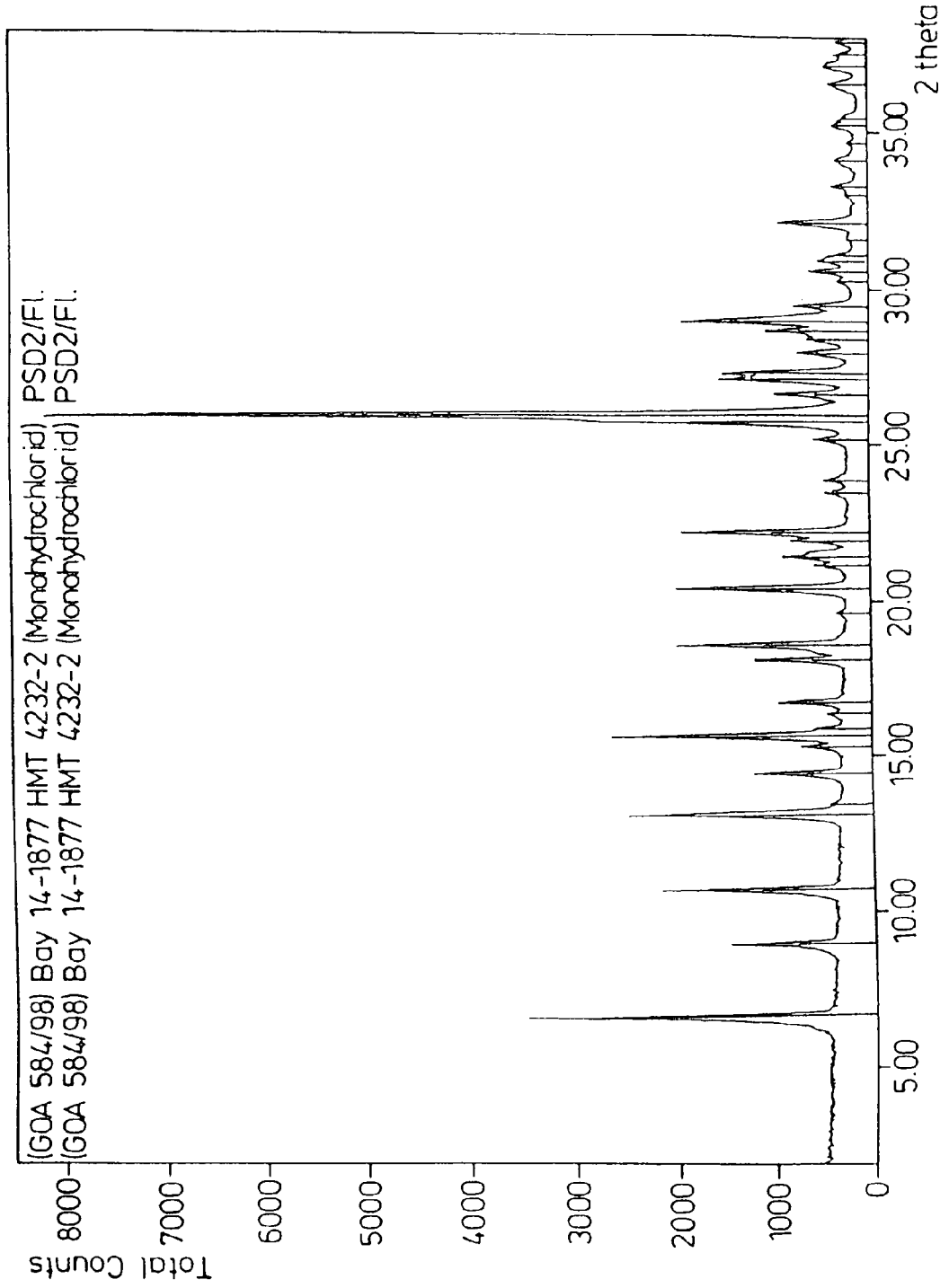
FIG. 1 shows the X-ray powder diffractogram of CCDC hydrochloride of the formula (IV).
Figure 2:
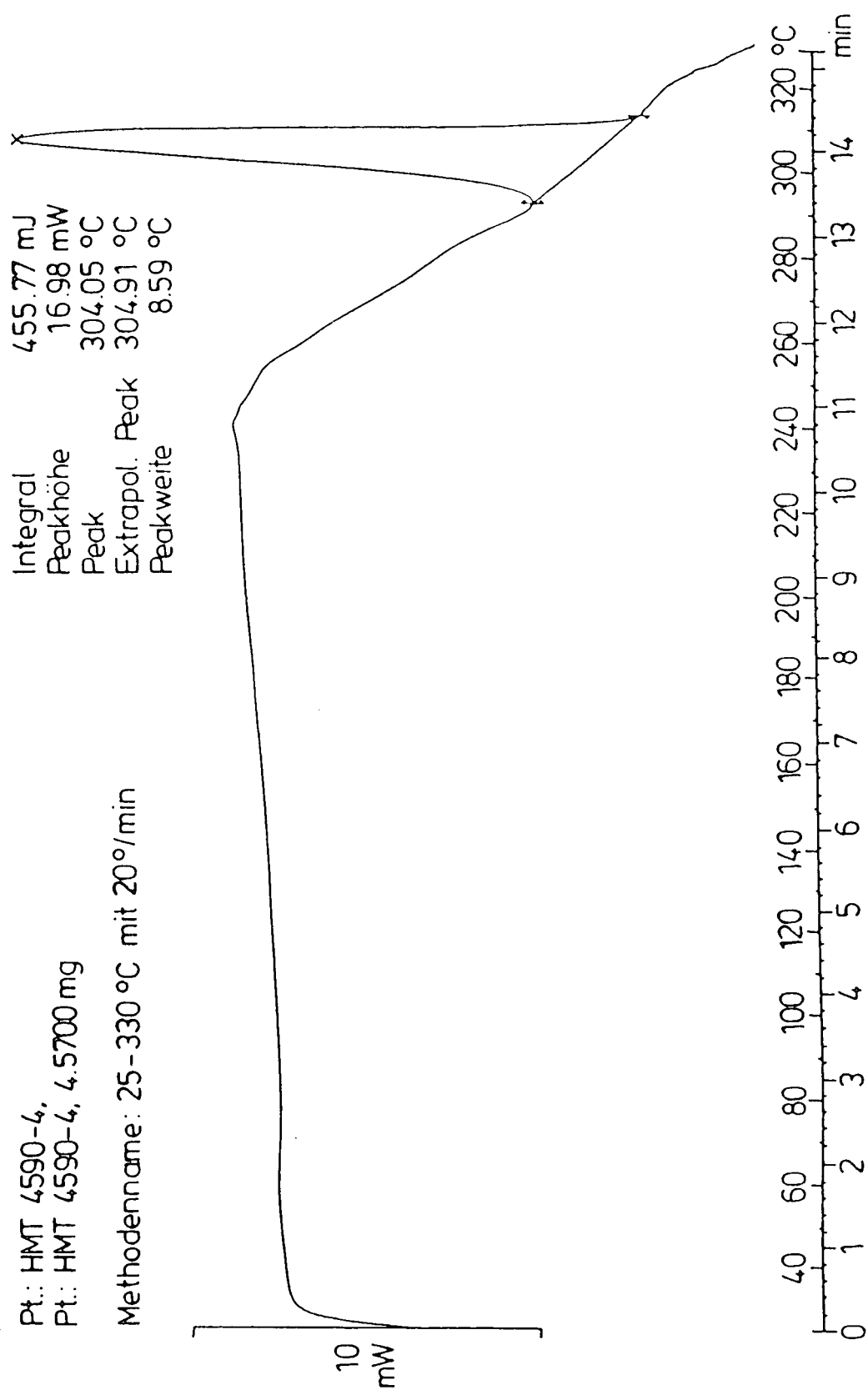
FIG. 2 shows the differential thermodiagram of the melting point, determined by DTA, of CCDC hydrochloride of the formula (IV) being from 305° C. to 307° C. (with decomposition).
Figure 3:
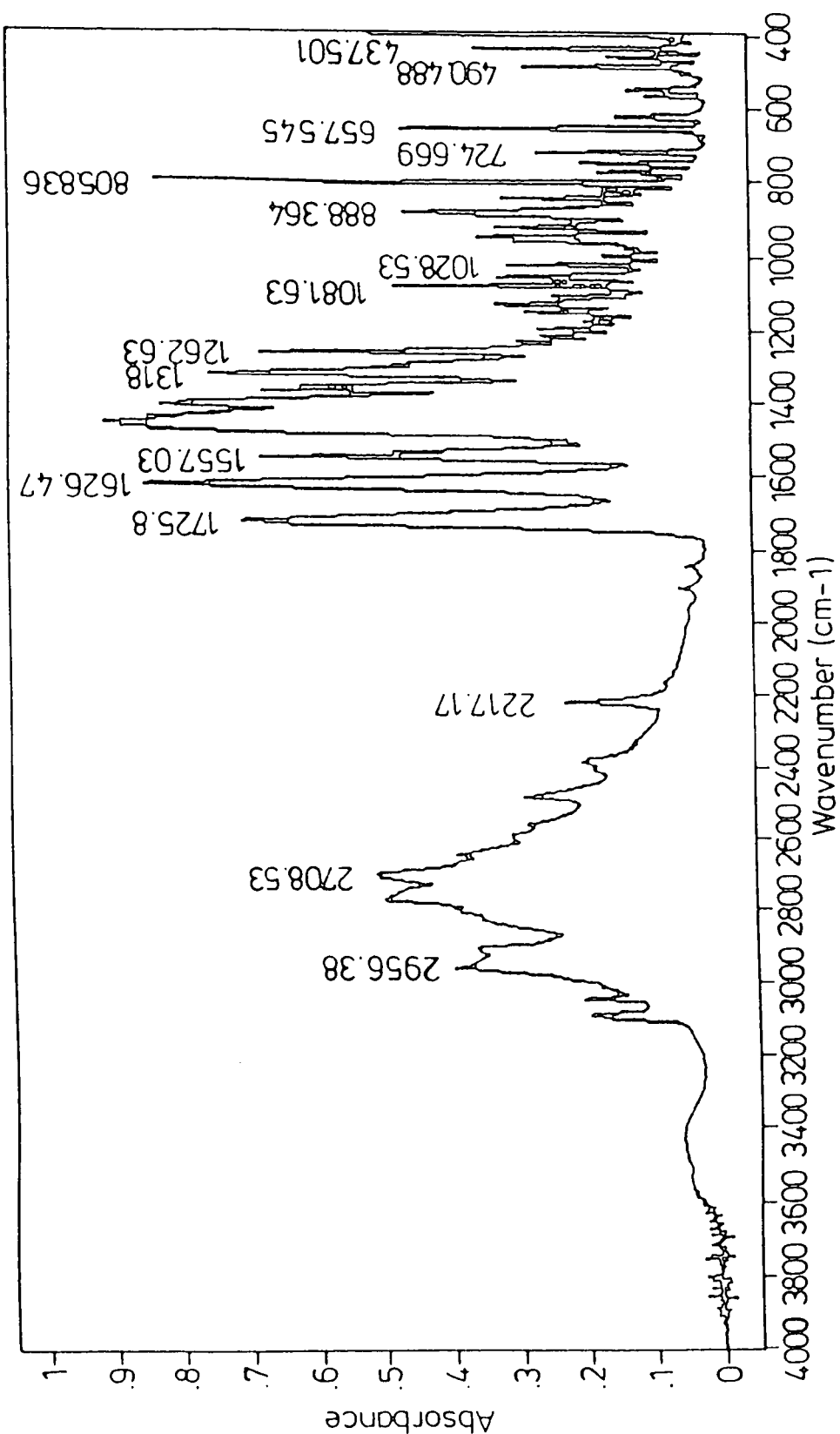
FIG. 3 shows the IR spectrum measured in KBr of CCDC hydrochloride of formula (IV).

The product has the X-ray powder diffractogram shown in FIG. 1, the differential thermodiagram shown in FIG. 1 and the IR spectrum shown in FIG. 3.

Preparation of CCDC semihydrochloride of the formula (VI)

Example 1

9.2 g of 7-chloro-8-cyano-1-cyclopropyl-6-fluoro-1,4-dihydro-4-oxo-3-quinoline-carboxylic acid are initially charged in a mixture of 30 ml of butanol, 18 ml of N-methyl-pyrrolidone and 4.85 g of Hünig base. The mixture is heated to reflux, and 4.17 g of (1S,6S)-2,8-diazabicyclo[4.3.0]nonane are then added dropwise. After the dropwise addition has ended, stirring under reflux is continued for 3 hours and the mixture is then allowed to cool to room temperature, and the solid is filtered off with suction, washed with a total of 20 ml of butanol and dried in a vacuum drying oven at from 60 to 70° C. until the weight remains constant.

This gives 8.54 g of a beige solid which has the X-ray powder diffractogram shown in FIG. 4 and the differential thermodiagram shown in FIG. 5.

Elemental analysis (calculated values for the CCDC semi-hydrochloride $C_{21}H_{22.5}Cl_{0.5}FN_4O_3$, molecular weight 414.658):

Chlorine: found 4.2% (calc. 4.275%).

Example 2

A mixture of 9.2 g of 7-chloro-8-cyano-1-cyclopropyl-6-fluoro-1,4-dihydro-4-oxo-3-quinolinecarboxylic acid, 60 ml of butanol and 4.85 g of Hünig base is heated to reflux. 4.17 g of (1S,6S)-2,8-diazabicyclo[4.3.0]nonane are added dropwise, and the mixture is then stirred under reflux for 3 hours. The solid is filtered off with suction at room temperature, washed with a total of 20 ml of butanol and dried until the weight remains constant. This gives 10.6 g of a beige solid whose differential thermodiagram corresponds to that of CCDC semihydrochloride of the formula (VI).

Elemental analysis (calculated values for the CCDC semihydrochloride $C_{21}H_{22.5}Cl_{0.5}FN_4O_3$, molecular weight 414.658):
Carbon: found 60.55% (calc. 60.83%)
Hydrogen: found 5.3% (calc. 5.23%)
Chlorine: found 4.2% (calc. 4.275%)
Nitrogen: found 13.5% (calc. 13.51%)
Oxygen: found 11.7% (calc. 11.58%).

Example 3

A mixture of 4.6 g of 7-chloro-8-cyano-1-cyclopropyl-6-fluoro-1,4-dihydro-4-oxo-3-quinolinecarboxylic acid, 15 ml of propanol, 9 ml of N-methyl-pyrrolidone and 2.42 g of Hünig base is heated to reflux. 2.08 g of (1S,6S)-2,8-diazabicyclo-[4.3.0]nonane are added dropwise, and the mixture is then stirred under reflux for 3 hours. The solid is filtered off with suction at room temperature, washed with a total of 10 ml of propanol and dried until the weight remains constant. This gives 4.6 g of a beige solid whose differential thermodiagram corresponds to that of CCDC semihydrochloride.

Elemental analysis (calculated values for the CCDC semihydrochloride $C_{21}H_{22.5}Cl_{0.5}FN_4O_3$, molecular weight 414.658):

Chlorine: found 4.3% (calc. 4.275%).

Example 4

A mixture of 4.6 g of 7-chloro-8-cyano-1-cyclopropyl-6-fluoro-1,4-dihydro-4-oxo-3-quinolinecarboxylic acid, 15 ml of isopropanol, 9 ml of N-methyl-pyrrolidone and 2.42 g of Hünig base is heated to reflux. 2.08 g of (1S,6S)-2,8-diazabicyclo-[4.3.0]nonane are added dropwise, and the mixture is then stirred under reflux for 3 hours. The solid is filtered off with suction at room temperature, washed with a total of 10 ml of isopropanol and dried until the weight remains constant. This gives 5.3 g of a beige solid.

Elemental analysis (calculated values for the CCDC semihydrochloride $C_{21}H_{22.5}Cl_{0.5}FN_4O_3$, molecular weight 414.658):

Chlorine: found 4.2% (calc. 4.275).

Example 5

A mixture of 4.6 g of 7-chloro-8-cyano-1-cyclopropyl-6-fluoro-1,4-dihydro-4-oxo-3-quinolinecarboxylic acid, 15 ml of 2-butanol, 9 ml of N-methyl-pyrrolidone and 2.42 g of Hünig base is heated to reflux. 2.08 g of (1S,6S)-2,8-diazabicyclo-[4.3.0]nonane are added dropwise, and the mixture is then stirred under reflux for 3 hours. The solid is filtered off with suction at room temperature, washed with a total of 10 ml of 2-butanol and dried until the weight remains constant. This gives 5.48 g of a beige solid whose differential thermodiagram corresponds to that of CCDC semihydrochloride of the formula (VI).

Elemental analysis (calculated values for the CCDC semihydrochloride $C_{21}H_{22.5}Cl_{0.5}FN_4O_3$, molecular weight 414.658):

Chlorine: found 4.2% (calc. 4.275%).

Example 6

A mixture of 4.6 g of 7-chloro-8-cyano-1-cyclopropyl-6-fluoro-1,4-dihydro-4-oxo-3-quinolinecarboxylic acid, 15 ml of isobutanol, 9 ml of N-methyl-pyrrolidone and 2.42 g of Hünig base is heated to reflux. 2.08 g of (1S,6S)-2,8-diazabicyclo-[4.3.0]nonane are added dropwise, and the mixture is then stirred under reflux for 3 hours. The solid is filtered off with suction at room temperature, washed with a total of 10 ml of isobutanol and dried until the weight remains constant. This gives 4.99 g of a beige solid whose differential thermodiagram corresponds to that of CCDC semihydrochloride of the formula (VI).

Elemental analysis (calculated values for the CCDC semihydrochloride $C_{21}H_{22.5}Cl_{0.5}FN_4O_3$, molecular weight 414.658):

Chlorine: found 4.2% (calc. 4.275%).

Example 7

A mixture of 4.6 g of 7-chloro-8-cyano-1-cyclopropyl-6-fluoro-1,4-dihydro-4-oxo-3-quinolinecarboxylic acid, 15 ml of tert-butanol, 9 ml of N-methyl-pyrrolidone and 2.42 g of Hünig base is heated to reflux. 2.08 g of (1S,6S)-2,8-diazabicyclo-[4.3.0]nonane are added dropwise, and the mixture is then stirred under reflux for 3 hours. The solid is filtered off with suction at room temperature, washed with a total of 10 ml of hot tert-butanol and dried until the weight remains constant. This gives 5.38 g of a beige solid whose differential thermodiagram corresponds to that of CCDC semihydrochloride of the formula (VI).

Elemental analysis (calculated values for the CCDC semihydrochloride $C_{21}H_{22.5}Cl_{0.5}FN_4O_3$, molecular weight 414.658):

Chlorine: found 4.2% (calc. 4.275%).

Example 8

A mixture of 4.6 g of 7-chloro-8-cyano-1-cyclopropyl-6-fluoro-1,4-dihydro-4-oxo-3-quinolinecarboxylic acid, 15 ml of 1-pentanol, 9 ml of N-methyl-pyrrolidone and 2.42 g of Hünig base is heated to reflux. 2.08 g (1S,6S)-2,8-diazabicyclo-[4.3.0]nonane are added dropwise, and the mixture is then stirred under reflux for 3 hours. The solid is filtered off with suction at room temperature, washed with a total of 10 ml of 1-pentanol and dried until the weight remains constant. This gives 3.0 g of a beige solid whose differential thermodiagram corresponds to that of CCDC semihydrochloride of the formula (VI).

Elemental analysis (calculated values for the CCDC semihydrochloride $C_{21}H_{22.5}Cl_{0.5}FN_4O_3$, molecular weight 414.658):

Chlorine: found 4.3% (calc. 4.275%).

Example 9

A mixture of 4.6 g of 7-chloro-8-cyano-1-cyclopropyl-6-fluoro-1,4-dihydro-4-oxo-3-quinolinecarboxylic acid, 15 ml of ethanol, 9 ml of N-methyl-pyrrolidone and 3.47 g of tributylamine is heated to reflux. 2.08 g of (1S,6S)-2,8-diazabicyclo[4.3.0]nonane are added dropwise, and the mixture is then stirred under reflux for 3 hours. The solid is filtered off with suction at room temperature, washed with a total of 10 ml of ethanol and dried until the weight remains constant. This gives 5.0 g of a beige solid whose differential thermodiagram corresponds to that of CCDC semihydrochloride of the formula (VI).

Elemental analysis (calculated values for the CCDC semihydrochloride $C_{21}H_{22.5}Cl_{0.5}FN_4O_3$, molecular weight 414.658):

Chlorine: found 4.2% (calc. 4.275%).

Example 10

A mixture of 4.6 g of 7-chloro-8-cyano-1-cyclopropyl-6-fluoro-1,4-dihydro-4-oxo-3-quinolinecarboxylic acid, 15 ml of ethanol, 9 ml of N-methyl-pyrrolidone and 2.16 g of N-ethylmorpholine is heated to reflux. 2.08 g of (1S,6S)-2,8-diazabicyclo-[4.3.0]nonane are added dropwise, and the mixture is then stirred under reflux for 3 hours. The solid is filtered off with suction at room temperature, washed with a total of 10 ml of ethanol and dried until the weight remains constant. This gives 5.4 g of a beige solid.

Elemental analysis (calculated values for the CCDC semihydrochloride $C_{21}H_{22.5}Cl_{0.5}FN_4O_3$, molecular weight 414.658):

Chlorine: found 4.3% (calc. 4.275%).

Example 11

A mixture of 4.6 g of 7-chloro-8-cyano-1-cyclopropyl-6-fluoro-1,4-dihydro-4-oxo-3-quinolinecarboxylic acid, 15 ml of propanol, 9 ml of N,N-dimethylformamide and 2.42 g of Hünig base is heated to reflux. 2.08 g of (1S,6S)-2,8-diazabicyclo-[4.3.0]nonane are added dropwise, and the mixture is then stirred under reflux for 3 hours. The solid is filtered off with suction at room temperature, washed with a total of 10 ml of propanol and dried until the weight remains constant. This gives 4.4 g of a beige solid.

Elemental analysis (calculated values for the CCDC semihydrochloride $C_{21}H_{22.5}Cl_{0.5}FN_4O_3$, molecular weight 414.658):

Chlorine: found 4.2% (calc. 4.275%).

What is claimed is:

1. Semi-hydrochloride of 8-cyano-1-cyclopropyl-7-(1S,6S-2,8-diazabicyclo[4.3.0]nonan-8-yl)-6-fluoro-1,4-dihydro-4-oxo-3-quinolinecarboxylic acid.

2. Semi-hydrochloride of 8-cyano-1-cyclopropyl-7-(1S,6S-2,8-diazabicyclo-[4.3.0]nonan-8-yl)-6-fluoro-1,4-dihydro-4-oxo-3-quinolinecarboxylic acid (CCDC semihydrochloride), having an X-ray powder diffractogram with the following reflection signals (2 theta) of high and medium intensity

| θ (2 Theta) |
| --- |
| 5.86 |
| 6.90 |
| 7.26 |
| 8.98 |
| 9.35 |
| 10.13 |
| 10.68 |
| 10.97 |
| 12.41 |
| 13.67 |
| 14.57 |
| 14.89 |
| 15.73 |
| 16.07 |
| 16.47 |
| 16.87 |
| 17.78 |
| 18.91 |
| 19.81 |
| 20.04 |
| 20.62 |
| 20.75 |
| 20.93 |
| 21.46 |
| 21.74 |
| 22.92 |
| 25.36 |
| 25.71 |
| 26.98 |
| 27.58 |
| 28.24 |
| 30.61 |

3. Semi-hydrochloride of 8-cyano-1-cyclopropyl-7-(1S,6S-2,8-diazabicyclo-[4.3.0]nonan-8-yl)-6-fluoro-1-1,4-dihydro-4-oxo-3-quinolinecarboxylic acid (CCDC semihydrochloride), having X-ray powder diffractogram with the following reflection signals (2 theta) of high and medium intensity

| 2 θ (2 Theta) |
| --- |
| 5.86 |
| 6.90 |
| 7.26 |
| 8.98 |
| 9.35 |
| 10.13 |
| 10.68 |
| 10.97 |
| 12.41 |
| 13.67 |
| 14.57 |
| 14.89 |
| 15.73 |
| 16.07 |
| 16.47 |
| 16.87 |
| 17.78 |
| 18.91 |
| 19.81 |
| 20.04 |
| 20.62 |
| 20.75 |
| 20.93 |
| 21.46 |
| 21.74 |
| 22.92 |
| 25.36 |
| 25.71 |
| 26.98 |
| 27.58 |
| 28.24 |
| 30.61 | and a melting point, determined by differential thermoanalysis (DTA), of from 278° C. to 280° C.

4. A process for preparing CCDC semihydrochloride according to claim 1, comprising reacting 7-halogeno-8-cyano-1-cyclopropyl-6-fluoro-1,4-dihydro-4-oxo-3-quinolinecarboxylic acid of the formula (II)

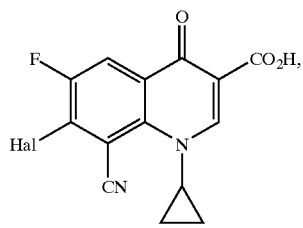

in which
Hal represents chlorine
and (1S,6S)-2,8-diazabicyclo[4.3.0]nonane of the formula (III)

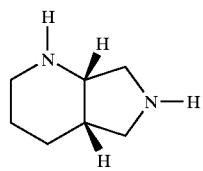

in the presence of a base in one of the following diluents or diluent mixtures:
a) aliphatic alcohols selected from the group consisting of butanol, isobutanol, 2-butanol, tert-butanol, and 1-pentanol,
b) mixture of aliphatic alcohols selected from the group consisting of propanol, isopropanol, butanol, isobutanol, 2-butanol, tert-butanol, and 1-pentanol with N-methylpyrrolidone,
c) mixture of propanol and N,N-dimethylformamide, or
d) mixture of ethanol with N-methyl-pyrrolidone with added tripropylamine, tributyl, N-ethylmorpholine, N-propylmorpholine and/or N-butylmorpholine base.

5. A process for preparing CCDC semihydrochloride according to claim 4, wherein the diluent used is an aliphatic alcohol selected from the group consisting of butanol, isobutanol, 2-butanol, tert-butanol, and 1-pentanol or that an aliphatic alcohol selected from the group consisting of propanol, isopropanol, butanol, isobutanol, 2-butanol, tert-butanol, and 1-pentanol is used as component of a diluent mixture.

6. A process for preparing CCDC semihydrochloride according to claim 4, wherein if an aliphatic alcohol selected from the group consisting of propanol, isopropanol, butanol, isobutanol, 2-butanol, tert-butanol, and 1-pentanol is used as component of a diluent mixture, N-methyl-pyrrolidone is simultaneously employed as a further diluent in a ratio of from 1:1 to 3:1.

7. Process for preparing CCDC semihydrochloride according to claim 5, wherein if propanol is used as component of a diluent mixture, N,N-dimethylformamide is simultaneously employed as further diluent in a ratio of from 1:1 to 3:1.

8. A pharmaceutical composition comprising, in addition to pharmaceutically acceptable auxilaries and excipients, CCDC semihydrochloride according to claim 1.

9. A method of preparing a pharmaceutical composition comprising combining a CCDC semihydrochloride according to claim 1 with one or more pharmaceutically acceptable auxiliaries and excipients.

10. A process for treating bacteria comprising applying to a human or animal an antibacterial composition containing CCDC semihydrochloride as defined in claim 1.

11. CCDC semihydrochloride according to claim 2, obtainable by reacting 7-halogeno-8-cyano-1-cyclopropyl-6-fluoro-1,4-dihydro-4-oxo-3-quinoline-carboxylic acid of the formula (II)

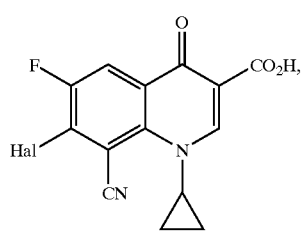

in which
Hal represents chlorine,
and (1S,6S)-2,8-diazabicyclo[4.3.0]nonane of the formula (III)

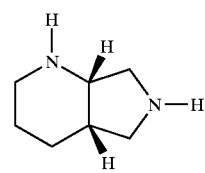

optionally in the presence of a base, in one of the following diluents or diluent mixtures:
a) aliphatic alcohols having at least four carbons,
b) mixture of aliphatic alcohols having at least three carbon atoms with N-methylpyrrolidone,
c) mixture of propanol and N,N-dimethylformamide, or
d) mixture of ethanol with N-methyl-pyrrolidone with added tripropylamine, tributylamine, N-ethylmorpholine, N-propylmorphine and/or N-butylmorphine base.

12. A process for preparing a CCDC semihydrochloride as defined in claim 2, wherein 7-halogeno-8-cyano-1-cyclopropyl-6-fluoro-1,4-dihydro-4-oxo-3-quinolinecarboxylic acid of the formula (II)

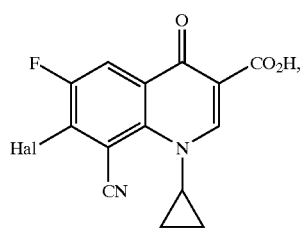

in which
Hal represents chlorine
and (1S,6S)-2,8-diazabicyclo[4.3.0]nonane of the formula (III)

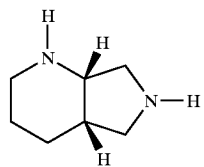

(III)

are reacted in the presence of a base in one of the following diluents or diluent mixtures:
 a) aliphatic alcohols having at least four carbon atoms,
 b) mixture of aliphatic alcohols having at least three carbon atoms with N-methylpyrrolidone,
 c) mixture of propanol and N,N-dimethylformamide, or
 d) mixture of ethanol with N-methyl-pyrrolidone with added tripropylamine, tributylamine, N-ethylmorpholine, N-propylmorpholine and/or N-butylmorpholine base.

13. A process for preparing a CCDC semihydrochloride as defined in claim 3, wherein 7-halogeno-8-cyano-1-cyclopropyl-6-fluoro-1,4-dihydro-4-oxo-3-quinolinecarboxylic acid of the formula (II)

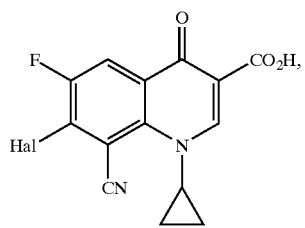

(II)

in which
Hal represents chlorine
and (1S,6S)-2,8-diazabicyclo[4.3.0]nonane of the formula (III)

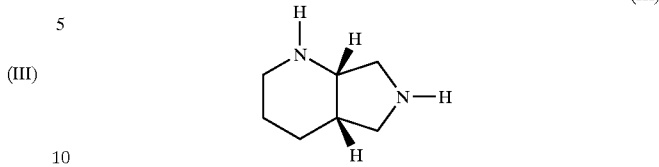

(III)

are reacted in the presence of a base in one of the following diluents or diluent mixtures:
 a) aliphatic alcohols having at least four carbon atoms,
 b) mixture of aliphatic alcohols having at least three carbon atoms with N-methylpyrrolidone,
 c) mixture of propanol and N,N-dimethylformamide, or
 d) mixture of ethanol with N-methyl-pyrrolidone with added tripropylamine, tributylamine, N-ethylmorpholine, N-propylmorpholine and/or N-butylmorpholine base.

14. A pharmaceutical composition comprising, in addition to pharmaceutically acceptable auxiliaries and excipients, CCDC semihydrochloride according to claim 2.

15. A pharmaceutical composition comprising, in addition to pharmaceutically acceptable auxiliaries and excipients, CCDC semihydrochloride according to claim 3.

16. A method of preparing a pharmaceutical composition comprising combining a CCDC semihydrochloride as defined in claim 2 with one or more pharmaceutically acceptable auxiliaries and excipients.

17. A method of preparing a pharmaceutical composition comprising combining a CCDC semihydrochloride as defined in claim 3 with one or more pharmaceutically acceptable auxiliaries and excipients.

18. A process for treating bacteria comprising applying to a human or animal an antibacterial composition containing CCDC semihydrochloride as defined in claim 2.

19. A process for treating bacteria comprising applying to a human or animal an antibacterial composition containing CCDC semihydrochloride as defined in claim 3.

* * * * *